US007597905B2

(12) United States Patent
Kuroda et al.

(10) Patent No.: US 7,597,905 B2
(45) Date of Patent: Oct. 6, 2009

(54) HOLLOW PROTEIN NANO-PARTICLES AND METHOD OF INTRODUCING SUBSTANCES INTO CELLS

(75) Inventors: Shun'ichi Kuroda, Osaka (JP); Katsuyuki Tanizawa, Osaka (JP); Masaharu Seno, Okayama (JP); Akihiko Kondo, Hyogo (JP); Masakazu Ueda, Tokyo (JP)

(73) Assignee: Beacle Inc., Okayama (JP)

( * ) Notice: Subject to any disclaimer, the term of this patent is extended or adjusted under 35 U.S.C. 154(b) by 0 days.

(21) Appl. No.: 10/220,125

(22) PCT Filed: Feb. 9, 2001

(86) PCT No.: PCT/JP01/00926

§ 371 (c)(1),
(2), (4) Date: Oct. 8, 2002

(87) PCT Pub. No.: WO01/64930

PCT Pub. Date: Sep. 7, 2001

(65) Prior Publication Data

US 2003/0092069 A1 May 15, 2003

(30) Foreign Application Priority Data

Feb. 28, 2000 (JP) ............................. 2000-052525
Feb. 7, 2001 (JP) ............................. 2001-031308

(51) Int. Cl.
*A61K 9/127* (2006.01)
*A61K 9/16* (2006.01)
*C12N 15/00* (2006.01)
(52) U.S. Cl. .................... 424/450; 424/491; 435/320.1
(58) Field of Classification Search ................. 435/7.2, 435/69.1, 348, 254.2, 320.1
See application file for complete search history.

(56) References Cited

U.S. PATENT DOCUMENTS 5,098,704 A * 3/1992 Valenzuela ............... 424/227.1
6,740,323 B1 * 5/2004 Selby et al. .............. 424/189.1

FOREIGN PATENT DOCUMENTS

| EP | 0201416 A1 | 11/1986 |
| EP | 0201416 B1 | 11/1986 |
| EP | 0 291 586 | 11/1988 |
| FR | 0 732 104 | 9/1996 |
| WO | 98/49195 | 11/1998 |
| WO | WO 9849195 A1 * | 11/1998 |
| WO | 99/61642 | 2/1999 |

OTHER PUBLICATIONS

Chiou, H.L. et al. "Altered antigeneicity of 'a' determinant variants of hepatitis B virus", 1997, J. of Gen. Virol., vol. 78: pp. 2639-2645.*
Schodel, F. et al. "Hybrid hepatitis B virus core antigen as a vaccine carrier moiety: I. Presentation of foreign epitopes", 1996, J. of Biotech., vol. 44: pp. 91-96.*
Ward, S. M. et al., "Development and Characterisation of Recombinant Hepatitis Delta Virus-like Particles", 2001, Virus Genes, vol. 23: p. 97-104.*
P. Pumpens et al., "Hepatitis B Core Particles as a Universal Display Model : a Structure-Function Basis for Development", FEBS Lett. Jan. 1999, vol. 442, No. 1, pp. 1-6.
F. Delpeyroux et al., "Insertions in the Hepatitis B Surface Antigen. Effect on Assembly and Secretion of 22-nm Particles from Mammalian Cells.", J. Mol. Biol. 1987, vol. 195, No. 2, pp. 343-350.
S. Kuroda et al., "Hepatitis B Virus Envelope L Protein Particles. Synthesis and Assembly in *Saccharomyces cerevisie*, Purification and Characterization.", J. Biol. Chem., 1992, vol. 263, No. 3, pp. 1953-1961.
H. Hanenberg et al., "Colocalization of Retrovirus and Target Cells on Specific Fibronectin Fragments Increases Genetic Transduction of Mammalian Cells.", Nat. Med. 1996, vol. 2, No. 8, pp. 876-882.
Delpeyroux et al., "Insertions in the hepatitis B surface antigen. Effect on assembly and secretion of 22-nm particles from mammalian cells", *J. Mol. Biol.*, vol. 195, No. 2, pp. 343-350, 1987 (Abstract only).
S Kuroda et al., "Hepatitis B virus envelope L protein particles", Journal of Biological Chemistry, vol. 267, No. 3, pp. 1953-1961, Jan. 25, 1992.
C Goldmann et al., "Molecular cloning and expression of major structural protein VP1 of the human polyomavirus JC virus: formation of virus-like particles useful for immunological and therapeutic studies", Journal of Virology, vol. 73, No. 5, pp. 4465-4469, May 1999.
K Miyamura et al., "Parvovirus particles as platforms for protein presentation", Proc. Natl. Acad. Sci., vol. 91, pp. 8507-8511, Aug. 1994.
T Li et al., "Expression and self-assembly of empty virus-like particles of hepatitis E virus", Journal of Virology, vol. 71, No. 10, pp. 7207-7213, Oct. 1997.
L Xing et al., "Recombinant hepatitis E capsid protein self-assembles into a dual-domain T=1 particle presenting native virus epitopes", Journal of Virology, vol. 265, pp. 35-45, 1999.
DJ Bertioli et al., "Transgenic plants and insect cells expressing the coat protein of arabis mosaic virus produce empty virus-like particles", Journal of General Virology, vol. 72, pp. 1801-1809, 1991.
K Dingle et al., "Human enteric *Caliciviridae*: the complete genome sequence and expression of virus-like particles from a genetic group II small round structured virus", Journal of General Virology, vol. 76, pp. 2349-2355, 1995.
C Martínez et al., "Production of porcine parvovirus empty capsids with high immunogenic activity", Vaccine, vol. 10, Iss. 10, pp. 684-690, 1992.

(Continued)

*Primary Examiner*—Michael Burkhart
(74) *Attorney, Agent, or Firm*—Wenderoth, Lind & Ponack, L.L.P.

(57) ABSTRACT

As a versatile means for specifically and safely transporting and transferring substances (genes, proteins, compounds, etc.) into target cells and tissues, hollow nano particles comprising a protein capable of forming particles (e.g., hepatitis B virus surface antigen protein), and a biorecognition molecule introduced therein, are provided.

3 Claims, 5 Drawing Sheets

OTHER PUBLICATIONS

H Chiou et al., "Altered antigenicity of 'a' determinant variants of hepatitis B virus", Journal of General Virology, vol. 78, pp. 2639-2645, 1997.
Supplementary European Search Report dated Nov. 30, 2007 issued in the corresponding European Application No. 01902820.8 of which the present application is the U.S. National Stage.
Yamada, et al., "Physicochemical and immunological characterization of hepatitis B virus envelope particles exclusively consisting of the entire L (pre-S1 + pre-S2 + S) protein," Vaccine, vol. 19, No. 23-24, Apr. 2001, pp. 3154-3163.
Database WPI Week 199846, Derwent Publications Ltd., 1998, AN 1998-535037, XP002459086.

* cited by examiner (a)

(b)

(c)

(a)                         (b)

(a) (b)

SEQUENCE LISTING

```
<160> NUMBER OF SEQ ID NOS: 27

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 1
cgacaaggca tgggaggcgg ccgcagccct caggctcag                         39

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Synthetic
      Oligonucleotide
```

<400> SEQUENCE: 2
ctgagcctga gggctgcggc cgcctcccat gccttgtcg                          39

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 3
ggggcggccg catgaactct gattccg                                       27

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 4
gggcggccgc cacgcagttc ccaccatttc                                    30

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 5
gggcggccgc ggccacttct ctaggtgc                                      28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 6
gggcggccgc cgtaaaacaa gtcaactc                                      28

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 7
ggggcggccg ccccgccttg cccgaggatg gc                                 32

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide -continued

<400> SEQUENCE: 8
gggcggccgc cgctcttagc agacattgga ag                32

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 9
ggctcgagat ggctctggag aagtctcttg                30

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 10
ccaagctttt aggtagagtc ctccacag                28

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 11
ggctcgagat gaaggaatcc cgggccaag                29

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 12
ccaagctttt aggtagagtc ctccacag                28

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 13
ggctcgagat ggttccaaaa ctgttcac                28

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 14 ccaagcttttt agatggtggt atccaggtg                                29

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 15
ggctcgagat gagaccccca cagtttacg                                 29

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 16
ccaagctttt agatggtggt atccaggtg                                 29

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 17
ggggtaccat gagatctttg ttgatcttg                                 29

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 18
ggccgcggtt aaatgtatac ccaaagac                                  28

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 19
gctgtacaaa accttcggac agaaactgca cttgtattcc                     40

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 20

```
ggaatacaag tgcagtttct gtccgaaggt tttgtacagc                               40
```

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 21

```
gcacgattcc tgctcgagga acctctatg                                          29
```

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 22

```
catagaggtt cctcgagcag gaatcgtgc                                          29
```

<210> SEQ ID NO 23
<211> LENGTH: 8
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 23

```
gcggccgc                                                                  8
```

<210> SEQ ID NO 24
<211> LENGTH: 6
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 24

```
ctcgag                                                                    6
```

<210> SEQ ID NO 25
<211> LENGTH: 6
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 25

```
aagctt                                                                    6
```

<210> SEQ ID NO 26
<211> LENGTH: 6
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 26

```
ggtacc                                                                    6
```

```
<210> SEQ ID NO 27
<211> LENGTH: 6
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 27 ccgcgg                                                                     6
```

HOLLOW PROTEIN NANO-PARTICLES AND METHOD OF INTRODUCING SUBSTANCES INTO CELLS

This application is a 371 of PCT/JP01/00926 filed Feb. 9, 2001.

TECHNICAL FIELD

The present invention relates to hollow nano particles, which comprise a protein capable of forming particles, to which a biorecognition molecule has been introduced. More particularly, the invention relates to hollow nano particles, which can be used as transporters for transferring substances into particular cells or tissues.

BACKGROUND ART

In recent years, in the field of medicine, active development of highly effective drugs, which act directly on the affected part with less side effect, is being carried out. Particularly, a method known as drug delivery system (DDS) has attracted a great deal of attention since it allows the specific transportation of effective components such as drugs to target cells or tissues, and enables the effective component to act at the target site.

Further, in the field of molecular cell biology, gene transfer to a particular cell is recognized as an essential technology and is being studied actively. Additionally, with the recent discoveries in the genetic background of various diseases by the progress of the Human Genomic Project, the realization of such highly specific methods for gene transfer would also enable application in the field of gene therapy.

As for the method for transferring a gene into cells, a method of incorporating a macromolecular form of gene by endocytosis (calcium phosphate method, lipotectamine method, etc.), and a method for inserting a gene into a cell by perforating the cell membrane using electric pulse stimulation (electroporation or gene gun method) are known, and being used generally in molecular biology experiments.

Although these methods are convenient, they may not readily be applied in vivo, because the site to which genes are introduced must be exposed surgically by the direct and physical wounding of the cells. In addition, it is difficult to attain a gene transfer efficiency close to 100%.

Alternatively, as a highly safe method of transferring a substance, the liposome method is known. This method can be applied to cells and tissues of a living body because it does not require the injuring of the cells. However, it is difficult to give high cell and tissue specificity to liposome, which is a simple lipid. Moreover, there is another problem that the gene transfer efficiency in vivo is much lower than the required value.

Recently, a new technique of gene transfer, which uses an infectious virus created by integrating the gene of interest into the virus DNA, has been developed. This technique can be applied to individuals with approximately 100% of the gene transfer efficiency, does not require the gene transfer site to be exposed, and thus, has attracted much attention as an epoch-making method: however, there is a serious problem that the gene is transferred to cells other than the target, because the virus infects a wide range of cells non-specifically. Moreover, there is a possibility that the virus genome itself is integrated into the chromosome to induce unexpected side reaction in the future. Therefore, the technique has not yet been used therapeutically in early stages of a disease, and at present, has been applied only to patients of terminal symptoms.

In view of the above situation, the present invention was made to solve the problems of the prior art. Accordingly, the purpose of the present invention is to provide a versatile method for the safe and specific transportation and transfer of a substance (gene, protein, compound, and the like) to a target cell or tissue.

DISCLOSURE OF THE INVENTION

As a means to solve the above-described problems, the present invention firstly provides a hollow nano particle, comprising a protein capable of forming a particle, and a biorecognition molecule introduced thereto.

Secondly, the present invention provides a hollow nano particle, comprising a protein particle obtained by expressing a protein in a eucaryotic cell, and a biorecognition molecule introduced thereto.

As further embodiments, the present invention thirdly provides the hollow nano particle of the second invention, wherein the eucaryotic cell is either yeast or genetically recombinant yeast, and fourthly, the hollow nano particle, wherein the eucaryotic cell is an insect cell.

Further, the present invention fifthly provides the hollow nano particle, wherein the protein capable of forming a particle is a hepatitis B virus surface antigen protein.

Furthermore, the present invention sixthly provides the hollow nano particle, wherein the hepatitis B virus surface antigen protein is one of which its antigenicity has been reduced.

The present invention also provides as additional embodiments, any of the above-described hollow nano particles, wherein seventhly, the biorecognition molecule is a cell function-regulating molecule, eighthly, an antigen, ninthly, an antibody, and tenthly, a sugar chain.

Eleventhly, the present invention further provides a transporter of substances, comprising any of the above-described hollow nano particles, and a substance that is to be introduced into cells incorporated therein.

The present invention also provides as additional embodiments, the transporter of substances, wherein twelfthly, the substance to be introduced is a gene, thirteenthly, a protein, fourteenthly, an RNase that shows cytotoxicity in the cell, and fifteenthly, a compound.

The present invention further provides a method of preparing the transporter of substances of any one of the eleventh to fifteenth invention, comprising sixteenthly, the insertion of the substance to the hollow nano particle of any one of the first to tenth invention by electroporation, seventeenthly, by ultra-sonication, eighteenthly, by simple diffusion, and nineteenthly, by using a charged lipid.

The invention also provides twentiethly, a method for transferring a substance into cells or tissues, which comprises the use of the hollow nano particles of any one of the first to tenth invention, or twenty-firstly, a method for transferring a substance into cells or tissues, which comprises the use of the transporter of substances of any one of the eleventh to fifteenth invention.

Moreover, twenty-secondly, the present invention provides a therapeutic method for treating diseases, which comprises transporting a substance to certain cells or tissues by using at least one of the above twentieth or twenty-first method of transferring a substance.

BRIEF DESCRIPTION OF THE DRAWINGS

FIG. 1 is a diagram, which shows each protein region of an HBsAg gene in the Examples of the present invention. 1 to 8 indicates the function of the respective moiety of the surface, antigen (1: release inhibition; 2: receptor; 3: sugar chain 1; 4: polymerized serum albumin receptor; 5: transmembrane; 6: stabilization; 7: sugar chain 2; 8: transmembrane low polymerization/secretion).

Figure 2:
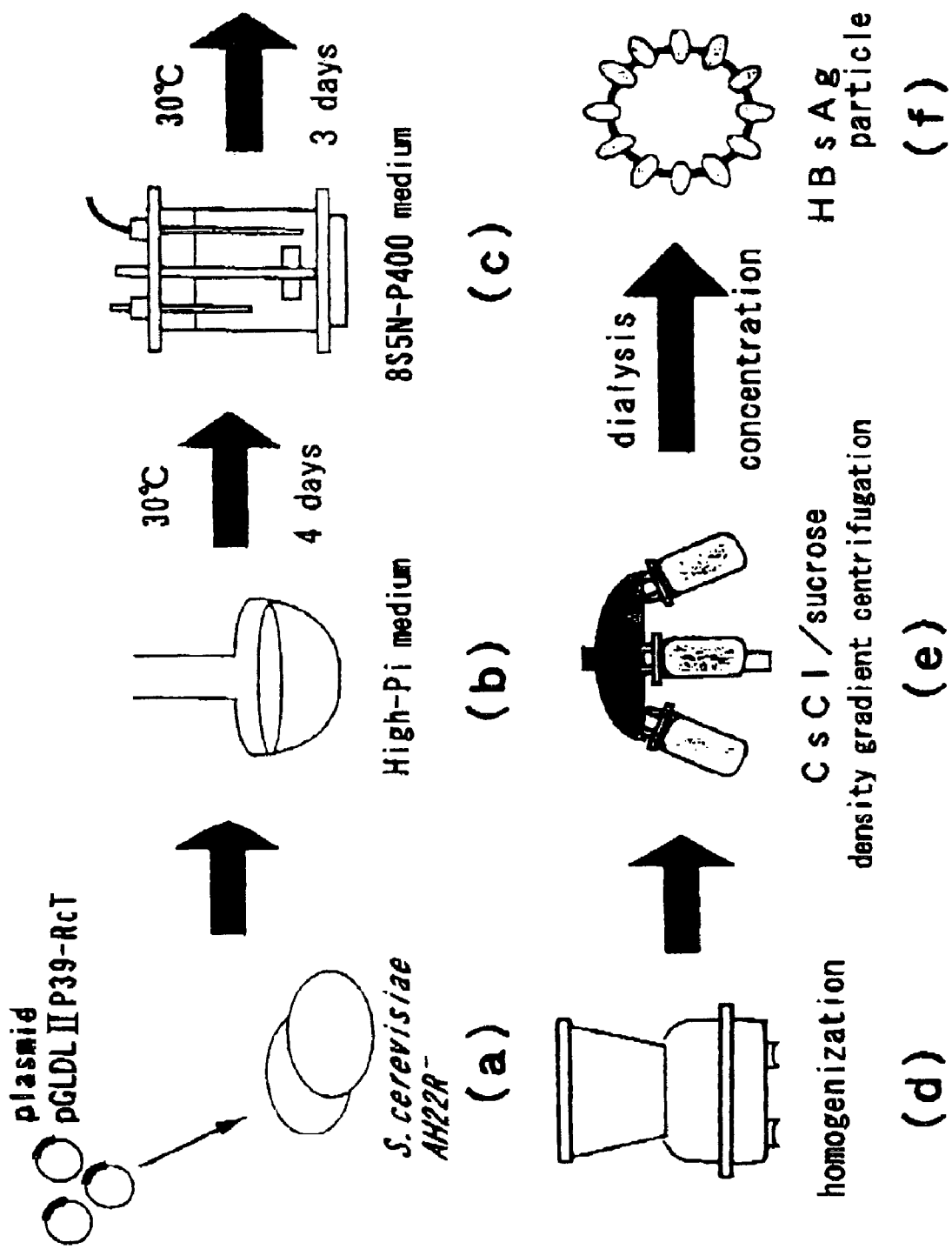

FIG. 2 is a diagram, which shows the expression and purification procedures for HBsAg particles using recombinant yeast in the Example of the present invention. Each represents: (a) Preparation of recombinant yeast; (b) Culture on a High-Pi medium; (c) Culture on an 8S5N-P400 medium; (d) Homogenization; (e) Density gradient centrifugation; and (f) HBsAg particles.

Figure 3:
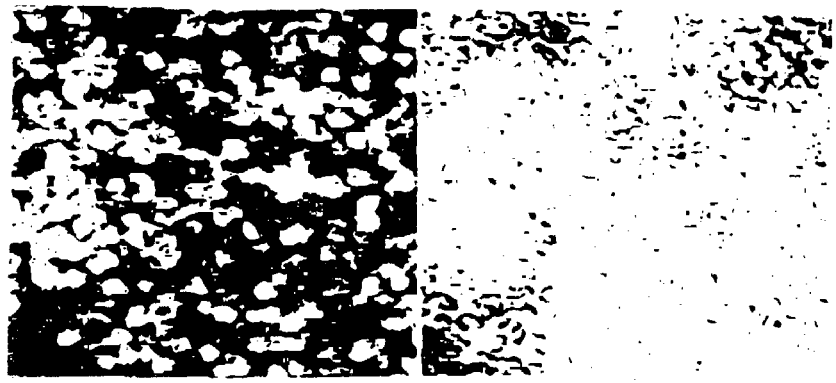
Figure 3:
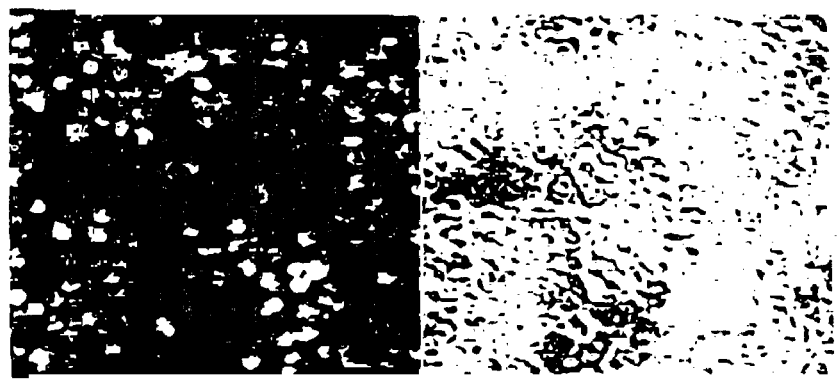
Figure 3:
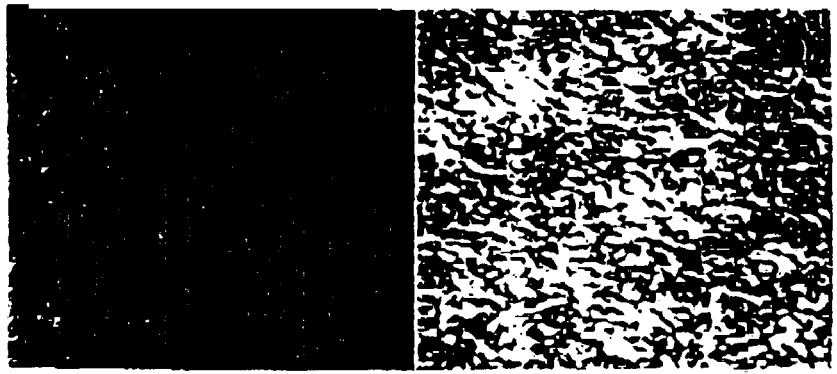

FIG. 3 shows a confocal laser fluorescent micrograph of HepG2, when HepG2 is in contact with HBsAg particles incorporating a GFP plasmid in the Example of the present invention. Each represents: (a) using HBsAg particles (plasmid: 8 ng); (b) Using lipid (liposome) (plasmid: 800 ng); (c) vector only (plasmid: 800 ng).

Figure 4:
Figure 4:
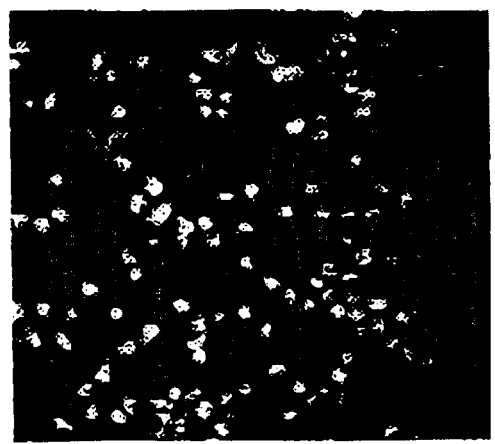

FIG. 4 shows a confocal laser fluorescent micrograph, indicating that GFP is also expressed in cells derived from human hepatogenic carcinoma (NUE) by HBsAg particles incorporating GFP plasmid. Each represents: (a) HepG2 cell and (b) NUE cell.

Figure 5:
Figure 5:

FIG. 5 shows a confocal laser fluorescent micrograph, indicating that HBsAg particles allow highly specific introduction of GFP into cells derived from human hepatic carcinoma (HuH-7). Each represents: (a) tumorigenic area of mice (positive fluorescence) to which cells derived from human hepatogenic carcinoma was transplanted; (b) normal mice liver (no fluorescence).

BEST MODE FOR CARRYING OUT THE INVENTION

The hollow nano particle of the present invention enables the specific transportation of a substance to a target cell or tissue by transferring a biorecognition molecule into a protein capable of forming particles. As a protein capable of forming particles, subviral particles obtained from a variety of viruses may be applied. Specifically, hepatitis B virus (HBV) surface antigen protein is exemplified.

The protein particle comprising a protein capable of forming a particle, include those obtained by expressing the protein in a eucaryotic cell. That is, when a protein capable of forming a particle is expressed in a eucaryotic cell, the protein is expressed and accumulated as a membrane protein on the membrane of the endoplasmic reticulum membrane and is released as particles. As the eucaryotic cell, yeast or recombinant yeast, and insect cells are applicable.

The present inventors have reported, as described in the following Examples, that when the L protein of the above-described HBV-surface antigen is expressed in the recombinant yeast, elliptical hollow particles of about 20 nm in diameter and about 150 nm in length, with large amounts of the protein embedded within the lipid bilayer membranes derived from yeast, were found from the expressed HBV-surface antigen L protein (*J. Bio. Chem.* Vol. 267, No. 3, 1953-1961, 1992). Since these particles contain no HBV genome or other HBV proteins, they do not act as viruses and are highly safe to the human body. In addition, the particles are effective as transporters for the specific transportation of substances to liver cells, because they display on their surface a hepatocyte-specific receptor that bear the high infectivity of HBV to liver cells.

Thus, the method of forming protein particles using recombinant yeast is preferred, because the particles are produced from soluble proteins in cell lysates at high efficiency.

On the other hand, insect cells are eucaryotic cells closer to higher animals than yeast, and are preferable for the efficient production of various proteins, because they can reproduce higher order structures such as sugar chains, which yeast cannot reproduce. Conventional system using insect cells utilized baculoviruses, and protein expression was accompanied by the expression of the virus, which led to cell death and lysis. Consequently, there was a problem that the continuous expression of the protein was required, and that the protein was degraded by protease released from the dead cells. Additionally, it was difficult to purify the protein expressed in a culture medium, because a large amount of fetal bovine serum existed in the medium. Recently, however, an insect cell system without the use of baculovirus, which may be cultured under serum-free conditions, was developed and marketed by invitrogen. Accordingly, by using such insect cells, it is possible to obtain protein particles that are purified easily, and in which high-order structure is reproduced.

In the protein hollow nano particles of the present invention, by converting the receptor on the surface of the particles obtained by the various methods described above into an optional recognition molecule, or by transferring a variety of substances (DNAs, RNAs, proteins, peptides, and drugs) into the particles, the transportation of substances to cells and tissues other than liver cells at a considerably high specificity becomes possible.

Of course, the proteins capable of forming particles are not limited to the above-described hepatitis B virus surface antigen and may be any kind of proteins as long as they are able to form particles; naturally occurring proteins derived from animal cells, plant cells, viruses, microorganisms, and the like, as well as various synthetic proteins are applicable. Further, for example, if there is a possibility that an antigenic protein of viral origin induces the generation of antibodies in the body, it may be used as a biorecognition molecule after modification to reduce its antigenicity.

As the biorecognition molecules that is introduced into a protein capable of forming particles, for example, cell function-regulating molecules, that is, molecules that regulates cell function such as growth factor, cytokines, etc.; cell or tissue-recognizing molecules such as cell surface antigen, tissue specific antigen, receptor, etc.; molecules derived from viruses or microorganisms; antibodies, sugar chains, lipids, and the like may preferably be used. These maybe chosen properly according to the target cells or tissues.

According to the present invention, a substance desired to be introduced into target cells or tissues (substance to be introduced into cells) is incorporated in the protein hollow nano particles as described above, to form a transporter of a substance that shows cell specificity. The substance to be introduced into cells, which is incorporated in the transporter, includes, for example, genes such as DNAs and RNAs, natural or synthetic proteins, oligonucleotides, peptides, drugs, natural or synthetic compounds, and the like.

Specifically, human RNase I (Jinno H., Ueda M., Ozawa S., Ikeda T., Enomoto K., Psarras K., Kitajima M., Yamada H., Seno M., *Life Sci.,* 1996, 58 (21), 1901-8), and RNase 3 (also known as ECP: Eosinophil Cationic Protein; Mallorqui-Fernandez G., Pous J., Peracaula R., Aymami J., Maeda T., Tada H., Yamada H., Seno M., de Llorens R., Gomis-Ruth F X, Coll M., *J. Mol. Biol.,* Jul. 28, 2000, 300 (5), 1297-307), which has been reported by the present inventors are applicable.

It Is known that these proteins show no cytotoxic activity outside the cell, but are cytotoxic when incorporated in the cells. Therefore, by using the transporters of the present invention incorporating RNase, proteins that exhibit selective cytotoxic activity against cells and tissues can be expressed forcibly, and is expected to be a new therapeutic method for cancer treatment.

Further, as a method of transferring such substances into the above-described hollow nano particles, various methods generally used in chemical or molecular-biological experimental techniques are applicable. For example, electroporation, ultrasonication, simple diffusion, or use of a charged lipid is preferably exemplified.

Hence, by using such protein hollow nano particles or transporters of substances, the in vivo or in vitro introduction of substances into cells or tissues are enabled. In addition, as exemplified above for RNase, the use of the protein hollow nano particles or transporters permits the introduction of a substance into certain cells or tissues for treatment of various diseases or as one step of such treatment.

Hereinafter, embodiments for carrying out the invention are described in further detail by the following examples and the attached figures. Of course, the invention is not limited in any way by the following examples. It is needless to say that various modifications of the embodiment are allowed.

EXAMPLES

Figure 1:
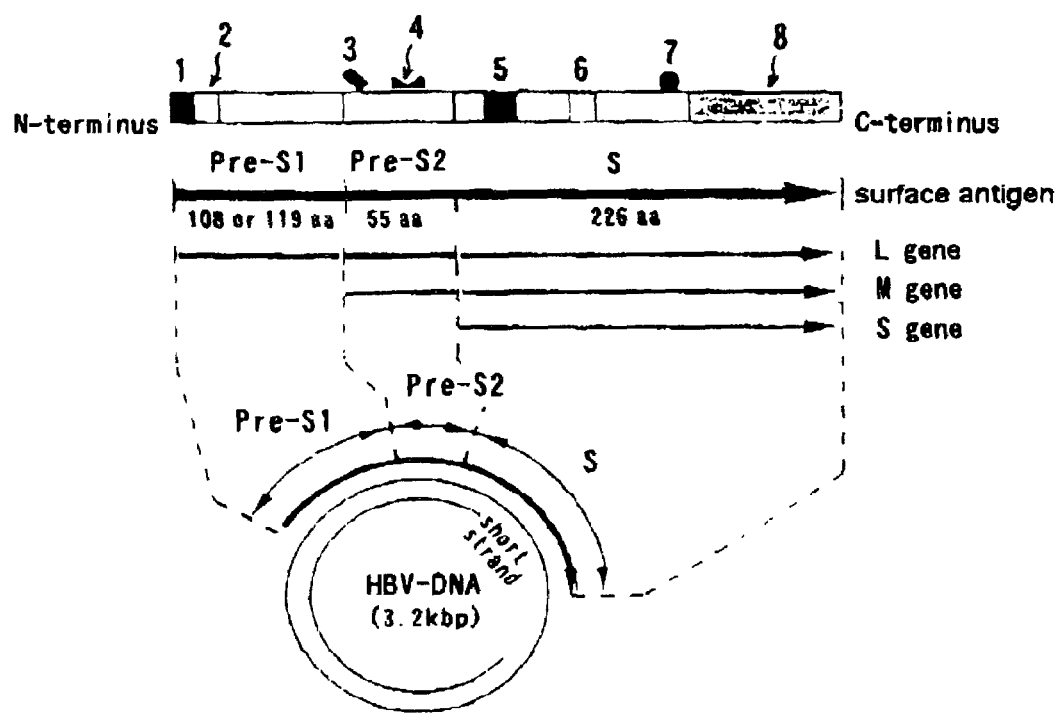

In the following Examples, HBsAg indicates a hepatitis B virus surface antigen. HBsAg, which is a coat protein of HBV, is classified into three types of protein, i.e., S protein, M protein and L protein, as indicated in FIG. 1. The S protein is an important coat protein common to all three proteins. M protein contains an added 55 amino acid residues (pre-S2 peptide) at the N-terminus of the S protein. Further, L protein contains 108 or 119 amino acid residues (pre-S1 peptide) added to the N-terminus of the M-protein.

The Pre-S regions of the HBsAg L protein (pre-S1, pre-S2) are both known to play an important role in the binding of HBV to the liver cells: Pre-S1 has a direct binding site for the liver cells, and pre-S2has a polymerized album in receptor which binds to the liver cells mediated by polymeric albumin in blood.

When HBsAg is expressed in eucaryotic cells, the HBsAg proteins are expressed and accumulated as membrane proteins on the endoplasmic reticulum membrane. L protein of HBsAg is aggregated, and released as particles into the lumen side in a budding form, while incorporating the endoplasmic reticulum membrane.

In the following Examples, L protein of HBsAg was used. FIG. 2 illustrates the expression and purification procedure for HBsAg particles as described in the following Examples.

Example A

Expression of HBsAg Particles by the Recombinant Yeast

The recombinant yeast carrying pGLDLIIP39-RcT (*Saccharomyces cerevisiae* AH22R strain) was cultivated in a synthetic medium High-Pi and 8S5N-P400 to express HBsAg L-protein particles, based on the method reported by the present inventors in *J. Bio. Chem.* Vol. 267, No. 3, 1953-1961 (1992) (FIGS. 2a and b).

From the recombinant yeast in the stationary growth phase (after about 72 hours), whole cell extracts were prepared using Yeast Protein Extraction Reagent (Pierce Chemical Co.), then separated by sodium dodecylsulfate-polyacrylamide gel electrophoresis (SDS-PAGE), and subjected to silver staining to identify HBsAg in the sample.

HBsAg was found to be a protein with a molecular weight of about 52 kDa.

Example B

Purification of HBsAg Particles from the Recombinant Yeast (1) The recombinant yeast (wet weight: 26 g) cultivated on the synthetic medium 8S5N-P400 was suspended in 100 ml of Buffer A (7.5 M urea, 0.1 M sodium phosphate, pH 7.2, 15 mM EDTA, 2 mM PMSF, 0.1% Tween 80) and homogenized by a BEAD-BEATER using glass beads. Then, the supernatant was recovered by centrifugation (FIGS. 2c and d).

(2) Subsequently, the supernatant was mixed with 0.75-fold volume of 33% (w/w) PEG 6000, and cooled over ice for 30 minutes. Then, the mixture was centrifuged (7000 rpm, 30 minutes) to recover pellets. The pellets were then re-suspended in Buffer A without Tween 80.

(3) The re-suspended solution was layered over CsCl solution of 10-40% gradient and subjected to ultracentrifugation at 28000 rpm for 16 hours. After centrifugation, the sediment was divided into 12 fractions, which were subjected to Western Blotting (primary antibody was anti-HBsAg monoclonal antibody) to identify the fraction containing HBsAg. Further, the fraction containing HBsAg was dialyzed in Buffer A without Tween 80.

(4) The dialysate (12 ml) obtained in (3) was layered over a sucrose solution of 5-50% gradient and subjected to ultracentrifugation at 28000 rpm for 16 hours. In the same manner as in (3), the fraction containing HBsAg after centrifugation was identified and dialyzed in Buffer A containing 0.85% NaCl instead of urea and Tween 80. ((2)-(4): FIG. 2e)

(5) The procedure of (4) was repeated and the sample after dialysis was concentrated using Ultra Filter Q2000 (Advantech Co.) and refrigerated at 4° C. until use. (FIG. 2f)

From the result of Western Blotting (3) after CsCl density equilibrium centrifugation, HBsAg was found to be a protein with a molecular weight of 52 kDa and an S-antigenicity. A total of about 24 mg of purified HBsAg particles were obtained from 26 g (wet weight) of the yeast cells derived from 2.5 L of culture medium.

The fractions obtained in the course of purification were analyzed by silver-staining SDS-PAGE. Further, to confirm that protease derived from yeast was removed by purification, the HBsAg particles obtained in (5) were incubated at 37° C. for 12 hours, then subjected to SDS-PAGE, and identified by silver staining.

As a result, it was confirmed that protease of yeast origin was completely removed by the overall purification process.

Example 1

Gene Transfer by HBsAg Particles in Human Liver Cancer Cell HepG2

Human liver cancer cell HepG2 in the logarithmic growth phase was inoculated on a 3.5 cm glass-bottom petri dish at $1\times10^5$ cells/well and cultivated overnight in a D-MEM medium containing 10% fetal bovine serum under 5% $CO_2$ at 37° C. On the following day, the HBsAg particles were mixed with green fluorescence protein expression plasmid (GFP expression plasmid pTB701-hGFP) and subjected to electroporation, then added to a HepG2 culture medium and cultivated in 5% $CO_2$ at 37° C. for 4 days.

The state of expression of GFP in HepG2 was observed with a confocal laser fluorescent microscope.

The gene transfer efficiency of HBsAg particles was determined by using HepG2. HBsAg particles containing GFP plasmid were prepared by an electroporation at a condition of 110V and 950 μF using a cuvette of 4 mm gap, and used to transform HepG2 cells, followed by cultivation in D-MEM under 5% $CO_2$ at 37° C. for 4 days.

FIG. 3 shows the confocal laser micrographs of HepG2. By comparing FIG. 3(a) with FIGS. 3(b) and (c), the efficiency shown in FIG. 3(a) was approximately 200 times that of FIG. 3(b), indicating that the transfer efficiency of GFP expression plasmid by HBsAg particles was very high.

Example 2

Gene Transfer by HBsAg Particles in Human Liver Cancer Cells Other than HepG2

According to the method as described in Example 1, HuH-7 (JCRB0403) and NUE (offered by Professor Takuji Tadakuma, Parasitology Lab, National Defense Medical College) were prepared as human hepatic cancer cells.

Further, as negative controls, human colon cancer cells, WiDr (ATCC CCL-218), HT29 (ATCC HTB-38) and SW1116 (ATCC CCL-233), human malignant melanoma cells SEKI (JCRB0620), and human squamous cell carcinoma A431 (JCRB9009) were cultivated separately on 3.5 cm glass bottom petri dishes, of which $10^5$ cells were infected by HBsAg particles containing the GFP expression plasmid (pEGFP-F (Clontech)) and cultivated continuously for 4 days. Then, the expression of GFP in the cells was observed with a confocal laser fluorescent microscope.

As a result, the degree of fluorescence in the Huh-7 and NUE cells was observed to be approximately equal to that of HepG2 cells (FIG. 4).

On the other hand, no GFP fluorescence was observed in the cells not derived from human liver.

Accordingly, it was demonstrated that, using the HBsAg particles of the invention, a gene could be introduced into human liver cells at the cultured cell level, in high efficiency and specificity.

Example 3

Gene Transfer by HBsAg Particles into Nude Mice with Human Liver Cancer Transplanted Thereto Tumor-bearing mice were prepared by subcutaneously injecting $1 \times 10^7$ cells of the human tumor strains (HuH-7 and WiDr) used in Example 2 to the bilateral dorsal cutis of nude mice (line: BALB/c nu/nu; microbiological quality: SPF; sex: male, 5 weeks old), and growing them for 2 to 6 weeks until the transplanted tumor developed into solid cancer of about 2 cm in diameter.

Ten μg of the HBsAg particles containing 2.5 μg of GFP expression plasmid (pEGFP-F) obtained according to the method described in Example 2 were administered intraperitoneally to mice with a 26G needle. Four days after administration, the mice were sacrificed, and the tumor portion, liver, spleen, kidney and intestine were removed, and their tissues were fixed and embedded using a resin-embedding kit for GFP (Technovit 7100).

Specifically, the fixation was performed by immersion in 4% neutralized formaldehyde and dehydration was carried out in 70% EtOH at room temperature for 2 hours, in 96% EtOH at room temperature for 2 hours, and in 100% EtOH at room temperature for 1 hour. Pre-immersion was carried out in an equal amount mixture of 100% EtOH and Technovit 7100 at room temperature for 2 hours. Then, the tissues were immersed in Technovit 7100 at room temperature within a period of 24 hours, taken out, and allowed to stand at room temperature and then at 37° C. for 1 hour for polymerization.

Sections were prepared according to conventional methods, and stained with hematoxin-eosin (conventional method of tissue staining); the fluorescence of GFP for the HBsAg particle-administered group and the non-administered group were compared under a fluorescent microscope (FIG. 5).

As shown in FIG. 5, fluorescence generated by GFP was observed on the tumor portions of the mice bearing cancer induced by HuH-7 cells derived from human liver cancer. However, no fluorescence was observed in the liver, spleen, kidney, and intestine simultaneously removed from the mice. Moreover, no fluorescence was seen in the tumor potion, liver, spleen, kidney, and intestine of mice bearing cancer induced by WiDr cells derived from human colon cancer, or in the control group to which no HBsAg particles were administered.

Accordingly, it was demonstrated that, using the HBsAg particles of the invention, a gene could be introduced into human liver cells in high efficiency and specificity, even in experimental animals. Therefore, the transporter of substances of the present invention was confirmed to be very effective.

Example C

Preparation of a Multi-purpose Type of HBsAg Particles (HBsAg-Null Particles) for Displaying a Biorecognition Molecule HBsAg particles are able to infect specifically to human liver cells, and the hepatocyte-recognizing site, which exhibit high infectivity, displayed on the surface of the particles is reported to be found in the 3rd to 77th amino acid residues of the pre-S1 region (Le Seyec J., Chouteau P., Cannie I., Guguen-Guillouzo C., Gripon P., *J. Virol.* 1999, March: 73(3), 2052-7).

Here, a method for preparing modified HBsAg particles (hereinafter referred to as HBsAg-Null particles), which lacks its high infectivity to liver cells and can display an optional biorecognition molecule on its surface while maintaining the capability of forming particles.

In the plasmid pGLDLIIP39-RcT described in Example A, in order to eliminate the genetic region coding the human liver cell-recognition site and to introduce the restriction enzyme NotI site (gcggccgc) (SEQ ID NO: 23) at the same time, PCR was carried out with QuickChange™ Site-Directed Mutagenesis Kit (Stratagene Co.) for the plasmid pGLDLIIP39-RcT, using the oligonucleotide of SEQ ID NO:1 and the oligonucleotide of SEQ ID NO:2 as PCR primers.

Specifically, using Pfu DNA polymerase (Stratagene Co.) as thermostable DNA polymerase, PCR was carried out under the schedule of: denaturation at 95° C. for 30 seconds; annealing at 55° C. for 1 minute; and polymerization reaction at 68° C. for 30 minutes, 30 cycles. Then, the PCR product was treated with restriction enzyme DpnI, and transformed into *Esaherichia coli* DH5α, after which the vector DNA was extracted from the resulting colony, and the mutated pGLDLIIP39-RcT plasmid (hereinafter, referred to as pGLDLIIP39-RcT (null)) was screened based on its nucleotide sequence.

According to the method described in Example A, the plasmid pGLDLIIP39-RcT (null) was transformed and cultivated in synthetic medium High-Pi and in 8S5N-P400, to express HBsAg-Null particles.

From recombinant yeast in the stationary growth phase (about 72 hours after starting the incubation), call extracts were prepared using an Yeast Protein Extraction Reagent (product of Pierce Chemical Co.), and then separated by SDS-PAGE, after which HBsAg-Null was identified by silver staining and Western blotting using an anti-S monoclonal antibody (Funakoshi).

Thus, HBsAg-Null was found to be a protein with a molecular weight of about 42 kDa.

In addition, according to the method described in Example B, about 3 mg of purified HBsAg-Null particles were obtained from the above-described cells (about 26 g) derived from 2.5 L of the culture medium. Measurement of S-antigenicity of HBsAg particles and HBsAg-Null particles (the degree of particle-formation) using the Auszyme II EIA kit (Dainabot Co. Ltd.) gave about equal values for both proteins.

Example 4

Gene Transfer with HBsAg-Null Particles in Cancer Cells of Human Origin

According to the method described in Example 2, the GFP expression plasmid (pEGFP-F (Clontech Co.)) was incorporated into the HBsAg-Null particles obtained in Example C, which lack the high infectivity to the liver cells, and are able to display an optional biorecognition molecule; gene transfer to HepG2 cells and a variety of cancer cells of human origin as described in Example 2 was performed for cultured cells.

However, no fluorescence by GFP was observed in any of the cells. This indicates that the high infectivity to cells is absent in HBsAg-Null particles.

Example 5

Gene Transfer by HBsAg-Null Particles into Nude Mice with Human Cancer Cells Transplanted Thereto According to the method described in Example 3, mice bearing cancer were prepared by transplanting of human tumor strains (HuH-7 and WiDr), and the HBsAg-Null particles containing GFP expression plasmid (pEGFP-F (Clontech Co.)) were administered. However, no fluorescence by GFP was observed in the tumor portions or in any of the major organs.

From these results, it was confirmed that the HBsAg-Null particles have no infectivity to any of the organs.

Example D

Preparation of HBsAg Particles Displaying an Epidermal Growth Factor (EGF)(HBsAg-EGF Particles)

The EGF receptor is known to be expressed on the surface of various cells, and to be particularly associated with the deterioration of certain cancers (esophageal cancer, colon cancer, etc.). Hence, HBsAg particles targeting the EGF receptor may provide an effective means for the treatment of cancer tissues that express the EGF receptor.

Herein, a method for preparing HBsAg particles of EGF-displaying type (HBsAg-EGF particles) based on the HBsAg-Null particles obtained by the method of Example C is described.

Using a cDNA fragment of EGF precursor of human origin (Bell G I, Fong N M, Stempien M M, Wormsted M A, Caput D, Ku L L, Urdea M S, Rall L B, Sanchez-Pescador R, *Nucleic Acids Res*. 1986, November, 11:14 (21), 8427-46) as a template, a gene fragment coding a mature human EGF region (53 amino acid residues) was amplified by PCR according to conventional methods.

The two PCR primers used were the oligonucleotide of SEQ ID NO.3 for sense and the oligonucleotide of SEQ ID NO.4 for antisense, which were both designed to contain the restriction enzyme NotI site (gcggccgc) (SEQ ID NO: 23) at the 5'-terminus.

After separation of the PCR product by agarose electrophoresis, the band containing the intended cDNA band (about 170 bp) was recovered, and sub-cloned to pCR2.1-TOPO vector (Invitrogen Co.) using TOPO TA Cloning kit (Invitrogen Co.). After confirming the nucleotide sequence, this was cleaved with the restriction enzyme NotI to recover the intended DNA fragment of about 170 bp, and using a TaKaRa Ligation kit ver.2 (TaKaRa Co.), cyclized together with pGLDLIIP39-RcT (null), which was first cleaved with the restriction enzyme NotI, after which it was transformed into *Escherichia coli* DH5α.

After screening by nucleotide sequence analysis, the fused plasmid in which the reading frame of the inserted EGF gene was identical to that of the HBsAg gene was selected and designated as pGLDLIIP39-RcT-EGF.

According to the method of Example A, the plasmid pGLDLIIP39-RcT-EGF was transformed and cultivated in the synthetic medium High-Pi and 8S5N-P400 to express HBsAg-EGF particles.

From the recombinant yeast in the stationary growth phase (72 hours after starting incubation), crude cell extracts were prepared using Yeast Protein Extraction Reagent (Pierce Chemical Co.), separated by SDS-PAGE, and subjected to silver staining and Western blotting using an anti-human EGF polyclonal antibody (Santa Cruz Co.) to identify the HBsAg-EGF.

Thus, HBsAg-EGF was found to be a protein with a molecular weight of about 50 kDa.

According to the method described in Example B, about 3 mg of the purified HBsAg-EGF particles were obtained from the above-described cells (about 26 g) derived from 2.5 L of the culture medium. The S-antiganicity (the degree of particle-formation) of HBsAg particles and HBsAg-EGF particles was measured using the Auszyme II EIA kit (Dainabot Co. Ltd.), which can only detect the particle structure of HBsAg. The same values were observed for both.

Therefore, it was demonstrated that HBsAg-EGF particles were obtained, as were the HBsAg particles.

Example 6

Gene Transfer with HBsAg-EGF Particles in Cancer Cells of Human Origin

According to the method described in Example 2, the GFP expression plasmid pEGFP-F vector (Clontech Co.) was incorporated into the HBsAg-EGF particles, and gene transfer to HepG2cells as well as a variety of human cancer cells described in Example 2 was performed for cultured cells.

Among them, strong fluorescence from GFP was observed in A431 cells, which expressed a large amount of EGF receptor on the surface.

Therefore, it was confirmed that the HBsAg-EGF particles possessed higher infectivity to cells that express EGF receptor. Further, it was demonstrated that a biorecognition function could be given arbitrarily to modified HBsAg particles at the cultured cell-level.

Example 7

Gene Transfer by HBsAg-EGF Particles into Nude Mice with Human Cancer Cells Transplanted Thereto Cancer-bearing mice transplanted with human tumor strains (A431, HuH-7, WiDr) were prepared according to the method described in Example 3, and the HBsAg-EGF particles containing a GFP expression plasmid (pEGFP-F (Clontech Co.)) was administered to them; strong fluorescence was observed at the tumor area from A431. On the other hand, no fluorescence from GFP was observed in the tumor areas from the other cells or in the major organs.

Accordingly, it was confirmed that the HBsAg-EGF particles are able to specifically infect cells that express considerable amounts of EGF receptor, and that the particles have no infectivity to major organs.

Therefore, it was demonstrated that the HBsAg-Null particles with an optional biorecognition molecule fused or added to them, are capable of specifically transporting substances to any desired tissue or organ.

Example E

Preparation of HBsAg Particles (HBsAg-BTC Particles) Displaying Betacellulin (BTC)

BTC belongs to the type of EGF family, but its expression site is different from that of EGF. Particularly, it has been found that BTC plays an important role in the differentiation of the β-cells of spleen Langerhans islet, which plays an important role in the blood sugar regulation mechanism. Accordingly, if HBsAg particles that target the BTC receptor could be prepared, they may be expected to be useful as an effective means for transporting substances to tissues expressing the BTC receptor for the treatment of diabetes mellitus caused by β-cells.

Here, a method for preparing HBsAg particles of the BTC-displaying type (HBsAg-BTC particles) based on the HBsAg-Null particles obtained by the method of Example C, is described.

Using a cDNA fragment of BTC precursor of human origin (Sasada R, Ono Y, Taniyama Y. Shing Y, Folkman J, Igarashi K; *Biochem. Biophys. Res. Commun.* Feb. 15, 1993: 190 (3), 1173-9) as a template, a gene fragment coding for a known site capable of binding to the BTC receptor (48 amino acid residues of GHSFR - - - VDLFY) was amplified by PCR according to conventional methods.

The two PCR primers used were the oligonucleotide of SEQ ID NO:5 for sense and the oligonucleotide of SEQ ID NO:6 for anti-sense, which were both designed to contain the restriction enzyme NotI site (gcggccgc) (SEQ ID NO: 23) at the 5'-terminus.

After separation of the PCR product by agarose electrophoresis, the band containing the intended cDNA band (about 160 bp) was recovered, and sub-cloned to cCR2.1-TOPO vector (Invitrogen Co.) using TOPO TA Cloning kit (Invitrogen Co.). After confirming its nucleotide sequence, this was cleaved with the restriction enzyme NotI to recover the intended DNA fragment of about 160 bp, and using a TaKaRa Ligation kit ver.2 (TaKaRa Co.), cyclized together with pGLDLIIP39-RcT (null), which was first cleaved with the restriction enzyme NotI, after which it was transformed into *Escherichia coli* DR5α. After screening by nucleotide sequence analysis, a fused plasmid in which the inserted BTC gene was identical to the HBsAg gene in the reading frame was screened and designated as pGLDLIIP39-RcT-BTC.

According to the method of Example A, the plasmid pGLDLIIP39-RcT-BTC was transformed and cultivated in a synthetic medium High-Pi and 8S5N-P400 to express HBsAg-BTC particles.

From the recombinant yeast in its stationary growth phase (72 hours after starting incubation), crude cell extracts were prepared using Yeast Protein Extraction Reagent (Pierce Chemical Co.), separated by SDS-PAGE, and subjected to silver staining and Western blotting using an anti-human BTC polyclonal antibody (prepared by Mr. Seno, Department of Technology, Okayama University) to identify the HBsAg-BTC.

Thus, HBsAg-BCT was found to be a protein with a molecular weight of about 50 kDa.

According to the method described in Example B, about 3 mg of the purified HBsAg-BTC particles were obtained from the above-described cells (about 26 g) derived from 2.5 L of the culture medium. The S-antigenicity of HBsAg particles and HBsAg-BTC particles (the degree of particle formation) was measured using Auszyme II EIA kit (Dainabot Co. Ltd.), which can only detect the particle structure of HBsAg. The same values were observed for both particles.

Example 8

Gene Transfer with HBsAg-BTC Particles in Cancer Cells of Human Origin

According to the method described in Example 2, a GFP expression plasmid (pEGFP-F (Clontech Co.)) was incorporated into the HBsAg-BTC particles, and gene transfer to rat pancreas cell AR42J expressing BTC receptor, human lung cancer cell H69 expressing no BTC receptor, as well as the various cancer cells of human origin described in Example 2 was performed at the cultured cell-level.

Among them, strong fluorescence by GFP was observed in AR42J cells which expressed a large amount of BTC receptor on the surface.

Thus, it was confirmed that the HBsAg-BTC particles have high infectivity against the BTC receptor expression cells.

Example F

Preparation of HBsAg Particles Displaying Basic Fibroblast Growth Factor (bFGF) (HBsAg-bFGF Particles)

In the growth of cancer tissues in individuals, it is known that a signal is sent by the cancer cells to the peripheral tissues to induce generation of blood vessels (angiogenesis). It is known that a variety of growth factors (also known as angiogenesis factors) are involved, among which bFGF plays the central role. It has also been reported that the bFGF receptor is enhanced in the peripheral tissues (Li V W, Folkerth R D, Watanabe H, Yu C, Rupnick M, Barnes P, Scott R M, Black P M, Sallan S E, Folkman J, *Lancet* 1994, July 9:344 (8915), 82-6).

Therefore, it is considered that if HBsAg particles targeting the bFGF receptor are prepared, they may be an effective means for transporting substances to tissues expressing the bFGF receptor, and therapy for effectively inducing inhibition of angiogenesis in the peripheral tissues of cancers.

Herein, a method for preparing HBsAg particles of bFGF-displaying type (HBsAg-bFGF particles) based on the HBsAg-Null particles obtained by the method of Example C, is described.

Using a cDNA fragment of bFGF precursor of human origin (Kurokawa T, Sasada R, Iwane M, Igarashi K, *FEBS Lett.* 1987, March 9:213 (1) 189-94) as a template, a gene fragment coding a known site capable of binding to the bFGF receptor (146 amino acid residues of PALPED - - - PMSAKS) was amplified by PCR according to conventional methods.

The two PCR primers used were the oligonucleotide of SEQ ID NO:7 for sense and the oligonucleotide of SEQ ID NO:8 for anti-sense, which were both designed to contain the restriction enzyme NotI site (gcggccgc) (SEQ ID NO: 23) at the 5'-terminus.

After separation of the PCR product by agarose electrophoresis, the band containing the intended cDNA band (about 450 bp) was recovered, and sub-cloned to cCR2.1-TOPO vector (Invitrogen Co.) using TOPO TA Cloning kit (Invitrogen Co.). After confirming its nucleotide sequence, this was cleaved with the restriction enzyme NotI to recover the intended DNA fragment of about 450 bp, and using a TaKaRa Ligation kit ver.2 (TaKaRa Co.), cyclized together with pGLDLIIP39-RcT (null), which was first cleaved with the restriction enzyme NotI, after which it was transformed into *Escherichia coli* DH5α. After screening by nucleotide sequence analysis, the fused plasmid in which the inserted bFGF gene was identical to the HBsAg gene in the reading frame was screened and designated as pGLDLIIP39-RcT-bFGF.

According to the method of Example A, the plasmid pGLDLIIP39-RcT-bFGF was transformed and cultivated in a synthetic medium High-Pi and in 8S5N-P400 to express HBsAg-bFGF particles.

From the recombinant yeast in its stationary growth phase (72 hours after starting incubation), crude cell extracts were prepared using Yeast Protein Extraction Reagent (Pierce Chemical Co.), separated by SDS-PAGE, and subjected to silver staining and Western blotting using an anti-bFGF monoclonal antibody 3H3 (Wako Pure Chemical Ind.) to identify the HBsAg-bFGF. Thus, HBsAg-bFGF was found to be a protein with a molecular weight of about 58 kDa.

According to the method described in Example B, about 2 mg of the purified HBsAg-bFGF particles were obtained from the above-described cells (about 26 g) derived from 2.5 L of the culture medium. The S-antigenicity of HBsAg particles and HBsAg-pFGF particles (the degree of particle formation) was measured using Auszyme II EIA kit (Dainabot Co. Ltd.), which can only detect the particle structure of HBsAg. The same values were observed for both particles.

Example 9

Gene Transfer with HBsAg-bFGF Particles in Cancer Cells of Human Origin

According to the method described in Example 2, a GFP expression plasmid (pEGFP-F (Clontech Co.)) was incorporated into the HBsAg-bFGF particles, and gene transfer to human breast cancer cell MDA-MB-231 expressing bFGF receptor, human squamous cell carcinoma A431 expressing no bFGF receptor, as well as the various cancer cells of human origin described in Example 2 was performed at the cultured cell-level.

Among them, strong fluorescence by GFP was observed in MDA-MB-231 cells, which expressed a large amount of bFGF receptor on the surface.

Thus, it was confirmed that the HBsAg-bFGF particles have high infectivity against the bFGF receptor expression cells.

Example G

Construction of Human RNase Expression Vector Incorporated in the HBsAg Particles Here, a vector that can express the above-described RNase in cells was constructed. First, using human RNase 1 gene (Seno, M., Futami, J., Kosaka, M., Seno, S. and Yamada, H., *Biochim. Biophys. Acta* 1218 (3), 466-468, 1994) as a template, a gene fragment coding human RNase 1 that contains a signal peptide (RO fragment) (156 amino acid residues) was amplified by PCR, using the oligonucleotides of SEQ ID NO:9 (containing XhoI site, ctcgag (SEQ ID NO: 24)) and SEQ ID NO:10 (containing HindIII site, aagctt (SEQ ID NO: 25)) as primers.

Next, using the human RNase 1 gene as a template, a gene fragment coding human RNase 1 that contains no signal peptide(RM fragment) (128 amino acid residues) was amplified by PCR, using the oligonucleotides of SEQ ID NO:11 (containing a XhoI site, ctcgag (SEQ ID NO: 24)) and SEQ ID NO:12 (containing a HindIII site, aagctt (SEQ ID NO: 25)) as primers.

In addition, using human ECP gene (Rosengerg H F, Ackerman S J and Tenen D G, *J. Exp. Med* 170 (1), 163-176, 1989) as a template, a gene fragment coding human ECP that contains a signal peptide (EO fragment) (160 amino acid residues) was amplified by PCR, using the oligonucleotides of SEQ ID NO:13 (containing a XhoI site, ctcgag (SEQ ID NO: 24)) and SEQ ID NO:14 (containing a HindIII site, aagctt (SEQ ID NO: 25)) as primers.

Further, by using the human ECP gene as a template, a gene fragment coding human ECP that contains no signal peptide (EM fragment) (133 amino acid residues) was amplified by PCR, using the oligonucleotides of SEQ ID NO:15 (containing a XhoI site, ctcgag (SEQ ID NO: 24)) and SEQ ID NO:16 (containing a HindIII site, aagctt (SEQ ID NO: 25)) as primers.

The resulting fragments RO, RM, EO and EM were then sub-cloned into pGEM-Teasy vector (Promega Co.), and after confirming the nucleotide sequences, the fragments were cleaved with EcoRI and HindIII and subjected to agarose electrophoresis to recover the DNA fragments containing the above fragments. On the other hand, the expression vector pTriEx-1 (Novagen Co.) was cleaved with EcoRI and HindIII and cyclized with each of the above fragments using TaKaRa Ligation kit ver.2 (TaKaRa Co.). The resulting plasmids were designated as pTriEx-1-RO, pTriEx-1-RM, pTriEx-1-EO and pTriEx-1-EM.

Example H

Cytotoxic Effect with the RNase Expression Vector in Cultured Cells

COS-7 cells derived from the kidney of African Green Monkey were inoculated in each well of a 16-well plate at $1 \times 10^4$ cells/well, and cultivated overnight in D-MEM containing 10% fetal bovine serum under 5% $CO_2$ at 37° C. The following day, the plasmids, pTriEx-1-RO, pTriEx-1-RM, pTriEx-1-EO and pTriEx-1-EM were distributed at 0, 0.2, 0.5, 1.0, and 5.0 µg each, and vigorously mixed with 3 µl of gene transfer lipid FuGene 6 (Roche), followed by the addition of 100 µl of serum-free D-MEM medium to each well.

The mixture was cultivated for two nights in D-MEM containing 10% fetal bovine serum under 5% $CO_2$ at 37° C. Then, 100 µl each of MTT solution [PBS (phosphate-saline buffer) containing 5 mg/ml MTT (Wako Pure Chemical)] was added to each well, and allowed to stand at 37° C. for 4 hours, followed by the addition of 1 ml of a solubilizer [0.04 N hydrochloric acid in isopropanol]. After shaking at room temperature for 1 hour, the absorption spectrum of the mixture was measured at 570 nm and 630 nm.

Each sample was divided into 3 parts, and the measured values were obtained by dividing the absorbance at 570 nm by that at 630 nm. The results are shown in Table 1.

TABLE 1

| DNA Amount (μg) | Survival Rate (%) | | | |
|---|---|---|---|---|
| | RO With signal | RM No signal | EO With signal | EM No signal |
| 0 | 100.0 | 100.0 | 100.0 | 100.0 |
| 0.2 | 87.9 | 87.8 | 97.4 | 93.3 |
| 0.5 | 81.3 | 77.7 | 80.8 | 94.9 |
| 1 | 77.3 | 84.9 | 86.0 | 89.0 |
| 5 | 69.2 | 79.7 | 70.0 | 96.7 |

Consequently, cytotoxicity-inducing ability was observed in all of the expression systems.

From these results, it may be expected that by incorporating these RNase expression vectors into the various protein hollow nano particles of the present invention, the above-described RNase may be introduced cell-specifically and exhibit cytotoxic effects in the cells, thereby providing an effective therapy for diseases.

Example I

Preparation of HBsAg Particles with Serum-free Cultured Insect Cells

Although the method of expressing HBsAg particles by recombinant yeast as described in Example A is a highly efficient method for preparing the HBsAg particles, in which approximately 40% of soluble proteins in the cells are converted into HBsAg, this method requires complicated operations such as those described in Example B, in order to obtain purified HBsAg particles. In addition, although yeast has a protein synthesis system such as the endoplasmic reticulum membrane that is suitable for the expression of proteins derived from higher animals, it is known that, because it is a lower eucaryotic organism, it cannot reproduce higher order structure such as sugar chain.

Hence, hereinafter, a method for preparing HBsAg particles by an insect cell system, which does not require baculovirus and enables serum-free culture, is described.

From the HBsAg expression plasmid pGLDLII39-RcT for yeast described in Example A, a chicken-derived lysozyme secretion signal peptide fusion-HBsAg gene was amplified by PCR, using the oligonucleotides of SEQ ID NO:17 (containing a KpnI site, ggtacc (SEQ ID NO: 26) and SEQ ID NO:18 (containing a SacII site, ccgcgg (SEQ ID NO: 27) as primers.

After separating the PCR products by agarose electrophoresis and recovering the intended cDNA band of about 1.3 kbp, it was sub-cloned into pCR2.1-TOPO (Invitrogen Co.) using TOPO TA Cloning kit (Invitrogen Co.) and transformed into *Escherichia coli* DH5α. The plasmid, in which the intended gene was integrated correctly, was screened by nucleotide sequence analysis, treated with KpnI and SacII, and separated by agarose electrophoresis to recover the KpnK-SacII fragment of about 1.3 kbp.

Subsequently, the above gene fragment was ligated and cyclized between the KpnI site and SacII site of the vector pIZT/V5-His (Invitrogen Co.) for stable expression of insect cells, using TaKaRa Ligation kit ver.2 (TaKaRa Co.).

After confirming its nucleotide sequence, the plasmid was designated as pIZT/V5-His-HBsAg. Similarly, a modified HBsAg gene was removed from the plasmid pGLDLIIP39-RcT (null) described in Example C and pGLDLIIP39-RcT-EGF described in Example D, inserted into pIZT/V5-His, and designated as pIZT/V5-His-null and pIZT/V5-His-EGF, respectively.

On the other hand, the insect cell High Five strain (BTI-TN-5B1-4; Invitrogen) was tamed from a fetal bovine serum-containing medium to a serum-free medium (Ultimate Insect Serum-Free Medium; Invitrogen) over a period of about 1 month. Then, pIZT/V5-His-HBsAg was transformed into the High Five strain tamed to the serum-free medium, using the gene-transfer lipid, Insectin-Plus (Invitrogen Co.). The transformant was cultivated in a serum-free medium at 27° C. for 48 hours, and then in a serum-free medium containing 400 μg/mL of the antibiotic zeocin (Invitrogen Co.) for 4 to 7 days, until the cells became confluent.

The supernatant was recovered by centrifugation at 1500× g, for 5 minutes, and the HBsAg particles expressed were measured by Auszyme II ETA kit (Dainabot Co. Ltd.), to confirm the expression of HBsAg particles.

Thus the resulting supernatant (1 L) was concentrated by ultrafiltration (the filter used was UK-200, ADVANTEC; exclusion molecular weight 200K) and then purified by an anion exchange column (DEAE-Toyopearl 650M; Toyo Soda), to obtain 2 mg of uniform HBsAg particles.

Example J

Preparation of HBsAg Particles with Reduced Antigenicity

HBsAg particles can evoke anti-HBsAg antibodies in human when inoculated. Therefore, modified HBsAg particles, in which the antigenicity of the major antigen S-protein was reduced, were prepared.

Specifically, a variant of HB virus isolated from a patient who was inoculated with HB vaccine but developed hepatitis B (Carman W F, Zanetti A R, Karayiannis P, Waters J, Manzille G, Tanzi E, Zuckerman A J, Thomas H G; *Lancet* Aug. 11, 1990; 336 (8711); 325-9; Chiou H L, Lee T S, Kuo J, Mau Y C, Ho M S, J *Gen Virol* 1997 October; 78 (Pt 10): 2639-45) was introduced into the HBsAg particles.

In order to substitute the 145th Gly residue of the S-protein Bite of the plasmid pGLDLIIP39-RcT described in Example A to an Arg residue (the mutation is indicated by an underline), two PCR primers coding 5'-GCTGTACAAAACCTTCGGACAGAAACTGCACTTGTATTCC-3' (SEQ ID NO: 19) and its complimentary sequence 5'-GGAATACAAGTGCAGTTTCTGTCCGAAGGTTTTGTACAGC-3' (SEQ ID NO: 20), were used to carry out PCR of the plasmid pGLDLIIP39-RcT using a QuickChange™ Site-Directed Mutagenesis Kit (Stratagene).

Specifically, as a thermostable DNA polymerase, Pfu DNA polymerase (Stratagene) was used, and the PCR schedule was: denaturation at 95° C. for 30 seconds; annealing at 55° C. for 1 minute; polymerization reaction at 68° C. for 30 minutes; repetition of 30 cycles. Thereafter, the PCR product was treated with the restriction enzyme DpnI and transformed into *Escherichia coli* DH5α, after which the vector DNA was extracted from the colonies generated, and the mutated pGLDLIIP39-RcT plasmid was screened according to its nucleotide sequence. (Hereinafter referred to as pGLDLIIP39-RcT (G145R)).

In the same manner as in Example A, the plasmid pGLDLIIP39-RcT (G145R) was transformed and cultivated in the synthetic medium High-Pi and 8S5N-P400 to express HBsAg (G145R) particles.

From the recombinant yeast in the stationary growth phase (72 hours after starting incubation), crude cell extracts were prepared using Yeast Protein Extraction Reagent (Pierce Chemical Co.), separated by SDS-PAGE, and subjected to silver staining and Western blotting using an anti-S monoclonal antibody (Funakoshi Co.) to identify the HBsAg (G145R).

Thus, HBsAg (G145R) was found to be a protein with a molecular weight of about 52 kDa.

According to the method described in Example B, about 20 mg of the purified HBsAg (G145R) particles were obtained from the above-described cells (about 26 g) obtained from 2.5 L of the culture medium. The S-antigenicity of HBsAg particles and HBsAg (G145R) particles was measured using the Auszyme II EIA kit (Dainabot Co. Ltd.), which can only detect the particle structure of HBsAg. The values were 1 for the former and 0.2. for the latter.

In order to substitute the 129th Gln residue of the S-protein site of the above-described plasmid pGLDLIIP39-RcT (G145R) to an Arg residue (the mutation is indicated by an underline), two PCR primers coding 5'-GCACGATTCCT-GCTCGAGGAACCTCTATG-3' (SEQ ID NO: 21) and its complimentary sequence 5'-CATAGAGGTTCCT CGAGCAGGAATCGTGC-3' (SEQ ID NO: 22), were used to carry out PCR for the plasmid pGLDLIIP39-RCT (G145R) using QuickChange™ Site-Directed Mutagenesis Kit (Stratagene).

Specifically, as a thermostable DNA polymerase, Pfu DNA polymerase (Stratagene) was used, and the PCR schedule was: denaturation at 95° C. for 30 seconds; annealing at 55° C. for 1 minute; polymerization reaction at 68° C. for 30 minutes; repetition of 30 cycles.

Thereafter, the PCR product was treated with the restriction enzyme DpnI and transformed into *Escherichia coli* DH5α, after which the vector DNA was extracted from the colonies generated, and the mutated plasmid pGLDLIIP39-RCT (G145R) (hereinafter referred to as pGLDLIIP39-RcT (Q129R, G145R)) was screened according to its nucleotide sequence.

In the same manner as in Example A, the plasmid pGLDLIIP39-RcT (Q129R, G145R) was transformed and cultivated in the synthetic medium High-Pi and 8S5N-P400 to express HBsAg (Q129R, G145R) particles.

From the recombinant yeast in the stationary growth phase (72 hours after starting incubation), crude cell extracts were prepared using Yeast Protein Extraction Reagent (Pierce Chemical Co.), separated by SDS-PAGE, and subjected to silver staining and Western blotting using an anti-S monoclonal antibody (Funakoshi Co.) to identify the HBsAg (Q129R, G145R).

Thus, HBsAg (Q129R, C145R) was found to be a protein with a molecular weight of about 52 kDa.

According to the method described in Example B, about 20 mg of the purified HBsAg (Q129R, G145R) particles were obtained from the above-described cells (about 26 g) separated from 2.5 L of the culture medium. The S-antigenicity of HBsAg particles and HBsAg (Q129R, G145R) particles was measured using Auszyme II EIA kit (Dainabot Co. Ltd.), which can only detect the particle structure of HBsAg. The values were 1 for the former and less than 0.01 for the latter.

As described above, it is apparent that the HBsAg (Q129R, G145R) particles have low antigenicity and can be applied as a stable and effective means for transporting substances, even in a living body.

INDUSTRIAL APPLICABILITY

As described above in detail, the present invention provides novel hollow nano particles, which may be used as a transporter for the specific transportation and introduction of a substance into cells or tissues. Although the hollow nano particles hold a strong infectivity towards particular cells or tissues, they are highly safe, since they contain no viral genome, and may accordingly be widely applied in gene therapy or as DDS. Additionally, they are highly useful in industry, because they can be produced using a large-scale production system.

The invention claimed is:

1. A transporter for transferring a substance into target cells or tissues, comprising a hollow nanoparticle obtained by expressing a hepatitis B virus surface antigen protein or mutant thereof capable of forming a particle in a eukaryotic cell, and incorporated therein is a substance to be introduced into the target cell or tissues, wherein the substance is selected from the group consisting of genes, oligonucleotides, natural or synthetic proteins peptides and drugs, wherein the substance is introduced into the transporter by simple diffusion, a charged lipid, ultrasonication or electroporation and wherein the expressed hepatitis B virus surface antigen or mutant thereof is the only hepatitis B virus-originated protein component of the hollow nanoparticle.

2. The transporter according to claim 1, wherein the hepatitis B virus surface antigen protein is a hepatitis B virus surface antigen L-protein.

3. The transporter according to claim 1, wherein the amino acid at position 129 of the S-protein site is substituted with arginine and the amino acid at position 145 of the S-protein is substituted with arginine.

* * * * *